(12) United States Patent
Oral et al.

(10) Patent No.: US 7,468,062 B2
(45) Date of Patent: *Dec. 23, 2008

(54) ATRIAL ABLATION CATHETER ADAPTED FOR TREATMENT OF SEPTAL WALL ARRHYTHMOGENIC FOCI AND METHOD OF USE

(75) Inventors: Hakan Oral, Carlsbad, CA (US); Randell L. Werneth, Carlsbad, CA (US); Thomas M. Castellano, Carlsbad, CA (US); Christopher G. Kunis, Carlsbad, CA (US)

(73) Assignee: Ablation Frontiers, Inc., Carlsbad, CA (US)

( * ) Notice: Subject to any disclaimer, the term of this patent is extended or adjusted under 35 U.S.C. 154(b) by 407 days.

This patent is subject to a terminal disclaimer.

(21) Appl. No.: 10/997,713

(22) Filed: Nov. 24, 2004

(65) Prior Publication Data
US 2006/0111701 A1 May 25, 2006

(51) Int. Cl.
*A61B 18/18* (2006.01)
(52) U.S. Cl. .................... 606/41; 607/101; 607/122
(58) Field of Classification Search .............. 606/41, 606/42, 45–50; 607/101, 102, 122
See application file for complete search history.

(56) References Cited

U.S. PATENT DOCUMENTS

| | | | |
|---|---|---|---|
| 3,516,412 A | 6/1970 | Ackerman | |
| 4,411,266 A | 10/1983 | Cosman | |
| 4,432,377 A | 2/1984 | Dickhudt | |
| 4,660,571 A | 4/1987 | Hess et al. | |
| 4,785,815 A | 11/1988 | Cohen | |
| 4,860,769 A | 8/1989 | Fogarty | |
| 4,869,248 A | 9/1989 | Narula | |
| 4,882,777 A | 11/1989 | Narula | |
| 4,896,671 A | 1/1990 | Cunningham et al. | |
| 4,920,980 A | 5/1990 | Jackowski | |
| 4,966,597 A | 10/1990 | Cosman | |
| 5,010,894 A | 4/1991 | Edhag | 128/785 |
| 5,016,808 A | 5/1991 | Heil | |
| 5,083,565 A | 1/1992 | Parius | |
| 5,156,151 A | 10/1992 | Imran | |
| 5,228,442 A | 7/1993 | Imran | |
| 5,239,999 A | 8/1993 | Imran et al. | |
| 5,255,679 A | 10/1993 | Imran | |
| 5,279,299 A | 1/1994 | Imran et al. | |
| 5,281,218 A | 1/1994 | Imran | |
| 5,324,284 A | 6/1994 | Imran | |
| 5,327,889 A | 7/1994 | Imran et al. | |
| 5,330,466 A | 7/1994 | Imran | |
| 5,342,295 A | 8/1994 | Imran | |

(Continued)

FOREIGN PATENT DOCUMENTS

AU 5200671 10/2005

(Continued)

*Primary Examiner*—Michael Peffley
(74) *Attorney, Agent, or Firm*—Shay Glenn LLP (57) ABSTRACT

An atrial ablation catheter with an electrode array particularly adapted to locate and ablate foci of arrhythmia which are required for sustained atrial fibrillation is provided. The array is easily deployed and retracted from the catheter, and presents a proximally oriented electrode array that can be pulled against the septal wall of the left atrium to engage the septal wall.

37 Claims, 7 Drawing Sheets

U.S. PATENT DOCUMENTS

| | | |
|---|---|---|
| 5,345,936 A | 9/1994 | Pomeranz et al. |
| 5,383,917 A | 1/1995 | Desai et al. |
| 5,391,147 A | 2/1995 | Imran et al. |
| 5,397,339 A | 3/1995 | Desai et al. |
| 5,400,783 A | 3/1995 | Pomeranz et al. |
| 5,404,638 A | 4/1995 | Imran et al. |
| 5,406,946 A | 4/1995 | Imran |
| 5,445,148 A | 8/1995 | Jaraczewski et al. |
| 5,462,545 A | 10/1995 | Wang |
| 5,465,717 A | 11/1995 | Imran et al. |
| 5,487,757 A | 1/1996 | Truckal et al. |
| 5,492,119 A | 2/1996 | Abrams |
| 5,507,802 A | 4/1996 | Imran |
| 5,509,411 A | 4/1996 | Littmann et al. |
| 5,527,279 A | 6/1996 | Imran |
| 5,533,967 A | 7/1996 | Imran |
| 5,545,193 A | 8/1996 | Fleischman et al. |
| 5,545,200 A | 8/1996 | West et al. |
| 5,558,073 A | 9/1996 | Pomeranz et al. |
| 5,575,810 A | 11/1996 | Swanson et al. |
| 5,578,007 A | 11/1996 | Imran |
| 5,582,609 A | 12/1996 | Swanson et al. |
| 5,588,964 A | 12/1996 | Imran et al. |
| 5,595,183 A | 1/1997 | Swanson et al. |
| 5,598,848 A | 2/1997 | Swanson et al. |
| 5,607,462 A | 3/1997 | Imran |
| 5,637,090 A | 6/1997 | McGee et al. |
| 5,645,064 A | 7/1997 | Littmann et al. |
| 5,656,029 A | 8/1997 | Imran et al. |
| 5,666,970 A | 9/1997 | Smith |
| 5,680,860 A | 10/1997 | Imran |
| 5,682,885 A | 11/1997 | Littmann et al. |
| 5,687,723 A | 11/1997 | Avital |
| 5,693,078 A | 12/1997 | Desai et al. |
| 5,697,928 A | 12/1997 | Walcott et al. |
| 5,699,796 A | 12/1997 | Littmann et al. |
| 5,706,809 A | 1/1998 | Littmann et al. |
| 5,711,298 A | 1/1998 | Littman et al. |
| 5,741,320 A | 4/1998 | Thornton et al. |
| 5,782,760 A | 7/1998 | Schaer |
| 5,782,828 A | 7/1998 | Chen et al. |
| 5,782,899 A | 7/1998 | Imran ......................... 607/122 |
| 5,800,482 A | 9/1998 | Pomeranz et al. |
| 5,827,272 A | 10/1998 | Breining et al. |
| 5,837,001 A | 11/1998 | Mackey |
| 5,860,920 A | 1/1999 | McGee et al. |
| 5,863,291 A | 1/1999 | Schaer |
| 5,871,523 A | 2/1999 | Fleischman et al. |
| 5,876,399 A | 3/1999 | Chia et al. |
| 5,882,333 A | 3/1999 | Schaer et al. |
| 5,885,278 A | 3/1999 | Fleischman |
| 5,891,027 A | 4/1999 | Tu et al. |
| 5,891,135 A | 4/1999 | Jackson |
| 5,891,137 A | 4/1999 | Chia et al. |
| 5,893,847 A | 4/1999 | Kordis |
| 5,895,355 A | 4/1999 | Schaer |
| 5,895,417 A | 4/1999 | Pomeranz et al. |
| 5,897,554 A | 4/1999 | Chia et al. |
| 5,904,680 A | 5/1999 | Kordis et al. ................... 606/41 |
| 5,906,605 A | 5/1999 | Coxum |
| 5,910,129 A | 6/1999 | Koblish et al. |
| 5,911,720 A | 6/1999 | Bourne et al. ................. 606/41 |
| 5,916,214 A | 6/1999 | Cosio et al. |
| 5,928,191 A | 7/1999 | Houser et al. |
| 5,931,835 A | 8/1999 | Mackey |
| 5,935,063 A | 8/1999 | Nguyen |
| 5,938,694 A | 8/1999 | Jaraczewski et al. |
| 5,951,471 A | 9/1999 | de la Rama et al. |
| 5,967,978 A | 10/1999 | Littmann et al. |
| 5,968,040 A | 10/1999 | Swanson et al. ............... 606/41 |
| 5,992,418 A | 11/1999 | de la Rama et al. |
| 5,997,532 A | 12/1999 | McLaughlin et al. |
| 6,001,093 A | 12/1999 | Swanson et al. |
| 6,001,095 A | 12/1999 | de la Rama et al. |
| 6,002,956 A | 12/1999 | Schaer |
| 6,029,091 A | 2/2000 | de la Rama et al. |
| 6,032,674 A * | 3/2000 | Eggers et al. ................. 128/898 |
| 6,042,580 A | 3/2000 | Simpson |
| 6,048,329 A | 4/2000 | Thompson et al. |
| 6,049,737 A | 4/2000 | Sherman et al. |
| 6,053,937 A | 4/2000 | Edwards et al. ............. 607/104 |
| 6,059,778 A | 5/2000 | Sherman et al. |
| 6,063,077 A | 5/2000 | Schaer |
| 6,063,082 A | 5/2000 | DeVore et al. ................. 606/45 |
| 6,068,629 A | 5/2000 | Haissaguerre |
| 6,070,094 A | 5/2000 | Swanson et al. |
| 6,071,274 A | 6/2000 | Thompson et al. |
| 6,071,279 A | 6/2000 | Whayne et al. |
| 6,071,282 A * | 6/2000 | Fleischman ................... 606/41 |
| 6,074,351 A | 6/2000 | Houser et al. |
| 6,086,581 A | 7/2000 | Reynolds et al. |
| 6,088,610 A | 7/2000 | Littmann et al. |
| 6,096,036 A | 8/2000 | Bowe et al. |
| 6,099,524 A | 8/2000 | Lipson |
| 6,106,522 A | 8/2000 | Fleischman et al. |
| 6,119,041 A | 9/2000 | Pomeranz et al. |
| 6,129,724 A | 10/2000 | Fleischman et al. |
| 6,141,576 A | 10/2000 | Littmann et al. |
| 6,146,379 A | 11/2000 | Fleischman et al. |
| 6,171,306 B1 | 1/2001 | Swanson et al. |
| 6,200,314 B1 | 3/2001 | Sherman et al. |
| 6,214,002 B1 | 4/2001 | Fleischman et al. |
| 6,216,043 B1 | 4/2001 | Swanson et al. |
| 6,216,044 B1 | 4/2001 | Kordis |
| 6,238,390 B1 | 5/2001 | Tu et al. |
| 6,241,666 B1 | 6/2001 | Pomeranz et al. |
| 6,241,724 B1 | 6/2001 | Fleischman et al. |
| 6,241,726 B1 | 6/2001 | Chia et al. |
| 6,241,754 B1 | 6/2001 | Swanson et al. |
| 6,245,067 B1 | 6/2001 | Tu et al. |
| 6,251,107 B1 | 6/2001 | Schaer et al. |
| 6,256,540 B1 | 7/2001 | Panescu et al. |
| 6,267,746 B1 | 7/2001 | Bumbalough |
| 6,290,697 B1 | 9/2001 | Tu et al. |
| 6,302,880 B1 | 10/2001 | Schaer |
| 6,309,385 B1 | 10/2001 | Simpson |
| 6,332,880 B1 | 12/2001 | Yang et al. |
| 6,332,881 B1 | 12/2001 | Carner et al. |
| 6,346,104 B2 | 2/2002 | Daly et al. |
| 6,353,751 B1 | 3/2002 | Swanson et al. |
| 6,360,128 B2 | 3/2002 | Kordis et al. |
| 6,371,955 B1 | 4/2002 | Fuimaono et al. |
| 6,379,352 B1 | 4/2002 | Reynolds et al. |
| 6,428,536 B2 | 8/2002 | Panescu et al. |
| 6,447,506 B1 | 9/2002 | Swanson et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest |
| 6,488,678 B2 | 12/2002 | Sherman et al. |
| 6,500,172 B1 | 12/2002 | Panescu et al. |
| 6,514,246 B1 | 2/2003 | Swanson et al. |
| 6,544,262 B2 | 4/2003 | Fleischman ................... 606/41 |
| 6,554,794 B1 | 4/2003 | Mueller et al. |
| 6,558,378 B2 | 5/2003 | Sherman et al. |
| 6,572,612 B2 | 6/2003 | Stewart et al. |
| 6,574,492 B1 | 6/2003 | Ben-Haim et al. |
| 6,607,505 B1 | 8/2003 | Thompson et al. |
| 6,607,520 B2 | 8/2003 | Keane |
| 6,628,976 B1 | 9/2003 | Fuimaono et al. |
| 6,632,223 B1 | 10/2003 | Keane |

| | | | | | | |
|---|---|---|---|---|---|---|
| 6,640,120 B1 | 10/2003 | Swanson et al. | CA | 2251041 C | 6/2006 | |
| 6,658,279 B2 | 12/2003 | Swanson et al. | EP | 0428812 B1 | 10/1997 | |
| 6,669,693 B2 | 12/2003 | Friedman | EP | 0598742 B1 | 8/1999 | |
| 6,702,811 B2 | 3/2004 | Stewart | EP | 0957794 B1 | 11/1999 | |
| 6,746,446 B1 | 6/2004 | Hill et al. | EP | 0879016 B1 | 10/2003 | |
| 6,805,131 B2 | 10/2004 | Kordis | EP | 1384445 B1 | 2/2006 | |
| 6,813,520 B2 | 11/2004 | Truckai et al. | EP | 1011437 B1 | 5/2006 | |
| 6,814,732 B2 | 11/2004 | Schaer | EP | 1207798 B1 | 6/2006 | |
| 6,830,576 B2 | 12/2004 | Fleischman et al. | EP | 1321166 B1 | 7/2006 | |
| 6,893,439 B2 | 5/2005 | Fleischman | EP | 1343427 B1 | 7/2006 | |
| 6,961,602 B2 | 11/2005 | Fuimaono et al. | EP | 1690564 A1 | 8/2006 | |
| 6,966,908 B2 | 11/2005 | Maguire et al. | EP | 0828451 B1 | 9/2006 | |
| 6,972,016 B2 | 12/2005 | Hill et al. | EP | 1014874 B1 | 12/2006 | |
| 7,025,766 B2 | 4/2006 | Whayne et al. | EP | 1455667 B1 | 1/2007 | |
| 7,029,471 B2 | 4/2006 | Thompson et al. | WO | WO 90/06079 | 6/1990 | |
| 7,047,068 B2 | 5/2006 | Haissaguerre | WO | WO 94/12098 | 6/1994 | |
| 7,048,734 B1 | 5/2006 | Fleischman et al. | WO | WO 96/10961 | 4/1996 | |
| 7,099,712 B2 | 8/2006 | Fuimaono et al. | WO | WO 96/34559 | 11/1996 | |
| 7,115,122 B1 | 10/2006 | Swanson et al. | WO | WO 96/34560 | 11/1996 | |
| 7,151,964 B2 | 12/2006 | Desai | WO | WO 96/34570 | 11/1996 | |
| 7,155,270 B2 | 12/2006 | Solis et al. | WO | WO 96/34653 | 11/1996 | |
| 7,163,537 B2 | 1/2007 | Lee et al. | WO | WO 97/17904 | 5/1997 | |
| 2001/0018608 A1 | 8/2001 | Panescu et al. | WO | WO 97/25917 | 7/1997 | |
| 2001/0020166 A1 | 9/2001 | Daly et al. | WO | WO 97/25919 | 7/1997 | |
| 2001/0039418 A1 | 11/2001 | Schaer | WO | WO 97/36541 | 10/1997 | |
| 2002/0065465 A1 | 5/2002 | Panescu et al. | WO | WO 97/40760 | 11/1997 | |
| 2002/0161422 A1 | 10/2002 | Swanson et al. | WO | WO 97/42996 | 11/1997 | |
| 2002/0165532 A1 | 11/2002 | Hill et al. | WO | WO 98/18520 | 5/1998 | |
| 2002/0198522 A1 | 12/2002 | Kordis | WO | WO 98/19611 | 5/1998 | |
| 2003/0093069 A1 | 5/2003 | Panescu et al. | WO | WO 98/26724 | 6/1998 | |
| 2003/0204186 A1 | 10/2003 | Geistert et al. | WO | WO 99/56649 | 11/1999 | |
| 2004/0116921 A1 | 6/2004 | Sherman | WO | WO 97/32525 | 2/2001 | |
| 2005/0015084 A1 | 1/2005 | Hill et al. | WO | WO 03/089997 | 10/2003 | |
| 2005/0065512 A1 | 3/2005 | Schaer | WO | WO 2005/065562 | 7/2005 | |
| 2005/0177146 A1 | 8/2005 | Sherman | WO | WO 2005/065563 | 7/2005 | |
| 2006/0089637 A1 | 4/2006 | Sherman et al. | WO | WO 2005/104972 | 11/2005 | |
| 2006/0106375 A1 | 5/2006 | Sherman | WO | WO 2006/017517 | 2/2006 | |
| 2006/0111700 A1 | 5/2006 | Sherman | WO | WO 2006/044794 | 4/2006 | |
| 2006/0111708 A1 | 5/2006 | Vanney et al. | WO | WO 2006/049970 | 5/2006 | |
| 2006/0189975 A1 | 8/2006 | Whayne et al. | WO | WO 2006/052651 | 5/2006 | |
| 2006/0206109 A1 | 9/2006 | Swanson | WO | WO 2006/052905 | 5/2006 | |
| 2006/0241366 A1 | 10/2006 | Falwell et el | WO | WO 2007/016123 | 2/2007 | |
| 2007/0027448 A1 | 2/2007 | Paul | WO | WO 2007/024785 | 3/2007 | |

FOREIGN PATENT DOCUMENTS

| | | | |
|---|---|---|---|
| CA | 2276755 C | 5/2006 | |

* cited by examiner

Fig. 1

Patch Electrode

Control System

SAGITTATE

Fig. 15 right wall of left atrium

US 7,468,062 B2

ATRIAL ABLATION CATHETER ADAPTED FOR TREATMENT OF SEPTAL WALL ARRHYTHMOGENIC FOCI AND METHOD OF USE

FIELD OF THE INVENTIONS

The inventions described below relate the field of atrial ablation.

BACKGROUND OF THE INVENTIONS

Atrial fibrillation is a form of arrhythmia, or irregular heartbeat, in which the atria (the two small upper chambers of the heart) quiver instead of beating effectively. While there are a number of variations of atrial fibrillation with different causes, they all involve irregularities in the transmission of electrical impulses through the heart. As a result of abnormalities in the heart's electrical impulses, the heart is not able to pump the blood out properly, and it may pool and clot. If a blood clot moves to an artery in the brain, AF can lead to stroke. AF is also associated with increased risks of congestive heart failure and cardiomyopathy. These risks warrant medical attention for patients with AF even if the symptoms are mild. Atrial fibrillation is the most common sustained heart rhythm disorder and increases the risk for heart disease and stroke, both leading causes of death in the United States. Over 2 million adults in the United States have been diagnosed with atrial fibrillation.

Various ablation techniques have been proposed to treat atrial fibrillation, including the Cox-Maze procedure, linear ablation of various regions of the atrium, and circumferential pulmonary vein ablation. Each of these techniques has its various drawbacks. The Cox-Maze procedure and linear ablation procedures are tedious and time-consuming, taking up to several hours to accomplish endocardially. Circumferential ablation is proving to lead to rapid stenosis and occlusion of the pulmonary veins, and of course is not applicable to treatment of the septal wall of the left atrium. The catheter mounted electrode arrays described in our co-pending patent application Kunis, et al., Atrial Ablation Catheter and Method of Use, U.S. App. Ser. No. 10/997,172 filed Nov. 22, 2004 provide for more efficient and effective treatment of atrial fibrillation. The treatment of the septal wall is facilitated with the devices and methods described below, which permit septal wall treatment from a percutaneous venous access route without the need to maneuver a distally facing electrode array in apposition to the septal wall.

SUMMARY

The devices and methods described below provide for a simplified approach to the treatment of atrial fibrillation with substantially improved efficacy and outcomes in patients with paroxysmal or persistent atrial fibrillation, especially for those arrhythmia originating from, or sustained by, arrhythmogenic foci located on the septal wall of the left atrium. An endocardial catheter with an electrode array particularly adapted to locate and ablate foci of arrhythmia which are required for sustained atrial fibrillation is provided. The array is easily deployed and retracted from the catheter, and presents a proximally oriented electrode array that can be pulled against the septal wall of the left atrium to engage the septal wall. A control system comprising an ECG analyzer and a RF power supply operates to analyze electrical signals obtained from the electrode array, determine if an arrhythmogenic focus is present in the area covered by the array, and supply RF power to appropriate electrodes to ablate the focus.

BRIEF DESCRIPTION OF THE DRAWINGS

FIG. 10b illustrates the meaning of the terminology which precisely defines the electrode array of FIGS. 10 and 10a.

DETAILED DESCRIPTION OF THE INVENTIONS

Figure 1:
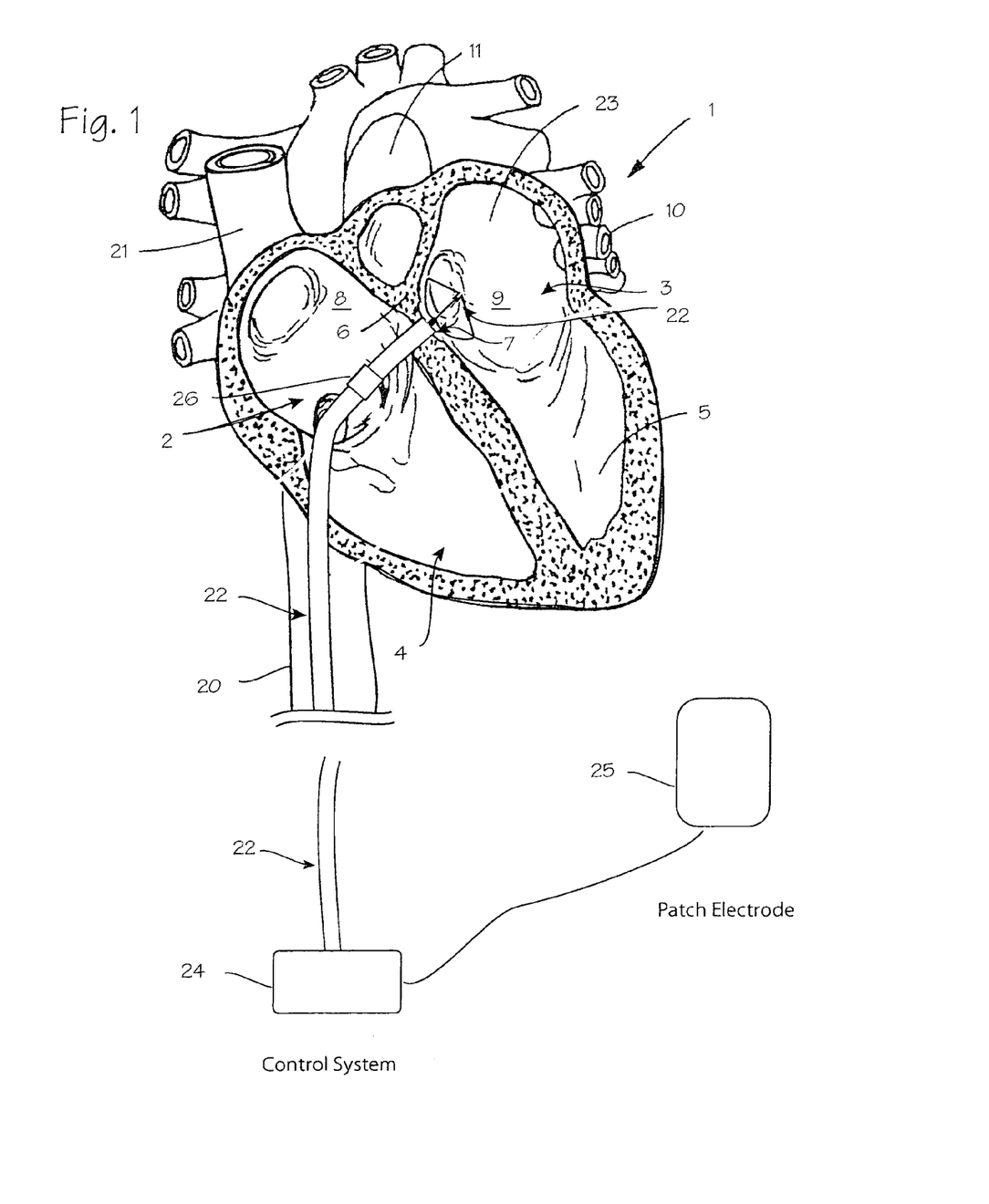
FIG. 1 illustrates the treatment to be accomplished with the devices and methods described below.

FIG. 1 illustrates the treatment to be accomplished with the devices and methods described below. FIG. 1 shows a cutaway view of the human heart 1, showing the major structures of the heart including the right atrium 2, the left atrium 3, the right ventricle 4, and the left ventricle 5. The atrial septum 6 separates the left and right atria. The fossa ovalis 7 is a small depression in the atrial septum which is easily punctured and easily heals. The percutaneous venous approach through the right atrium and the fossa ovalis is the preferred access pathway to the left atrium. In a patient suffering from atrial fibrillation, aberrant electrically conductive tissue may be found in the atrial walls 8 and 9, including the septal wall surrounding the fossa ovalis, as well as in the pulmonary veins 10 and pulmonary arteries 11. These areas of aberrant electrically conductive tissue, referred to as arrhythmogenic foci, drivers or rotors, cause or sustain atrial fibrillation. Ablation of these areas is an effective treatment for atrial fibrillation. Though circumferential ablation of the pulmonary veins cures the arrhythmia which originates in the pulmonary veins, it often results in rapid stenosis of the pulmonary veins. Ablation of foci, rotors or drivers on atrial walls, however, may prevent the propagation of any aberrant electrical activity that originates in the pulmonary veins, originates in other regions of the atrial wall, or originates on the septal wall itself.

To accomplish ablation of the septal wall of the left atrium, a catheter is inserted into the atrium, preferably through the inferior vena cava 20, as shown in the illustration, or through the superior vena cava 21, into the right atrium and then into left atrium. When passing into the left atrium, as illustrated, the catheter penetrates the fossa ovalis (a trans-septal puncture will facilitate the crossing). The catheter 22 carries a distal electrode array 23 into the atrium, and this electrode array is adapted to be pulled into contact with the section of the atrial wall surrounding the fossa ovalis. The electrode array is electrically connected to circuitry in a control system 24 which is operable to analyze electrical signals detected by the electrodes and pass RF current through the electrodes and heart tissue to ablate the tissue. A surface electrode 25 is mounted on the patient's body (typically on the back) to permit use of the electrodes in monopolar modes. A return electrode 26 may also be provided on the catheter 22, proximal to the electrode array. Using the catheter, an electrophysiologist will map regions of the septal wall of the left atrium and apply energy through the catheter to ablate any arrhythmogenic foci which are identified in the mapping procedure. The procedure may be repeated as necessary on the septal wall, rotating the array if necessary, to ablate all detected foci.

Figure 2:
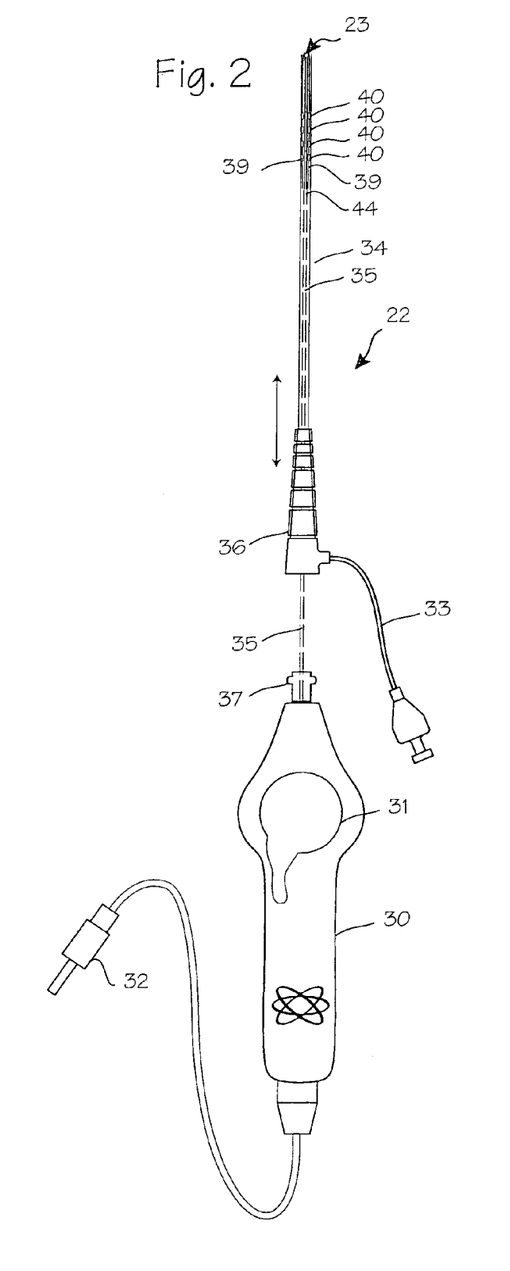
FIG. 2 illustrates an atrial sensing and ablation catheter with an expandable electrode array constrained within an outer catheter tube.

FIG. 2 illustrates an atrial sensing and ablation catheter 22 with an expandable electrode array. The catheter comprises a handle 30 with a steering control knob 31, electrical connector 32 and side-arm connector 33. The electrical connector is used to connect the catheter to the control box. An outer catheter tube 34 is slidably mounted on the inner catheter tube 35, and they may be releasably secured to each other by sliding the proximal portion of the outer catheter sheath strain relief 36 over the cylindrical detent 37 which is fixed to the handle. The side arm connector is used as a flushing port, to allow the flushing of debris and blood from the space between the inner and outer catheter tubes. The electrode array 23 is fixed to the inner catheter tube 35, and is restrained within the distal portion of the outer catheter tube 34.

Figure 3:
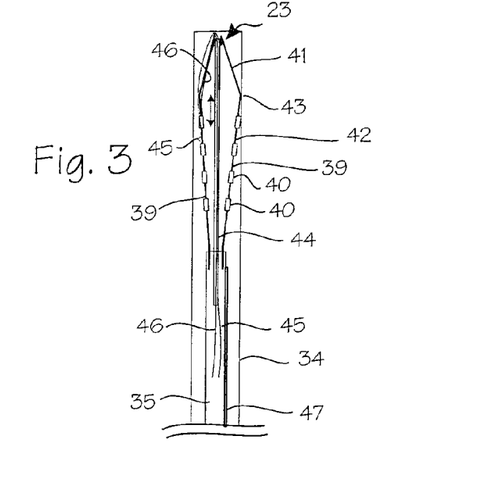
FIG. 3 is an enlarged view of the distal portion of the catheter of FIG. 2.
Figures 5, 6, 6A, 6B:
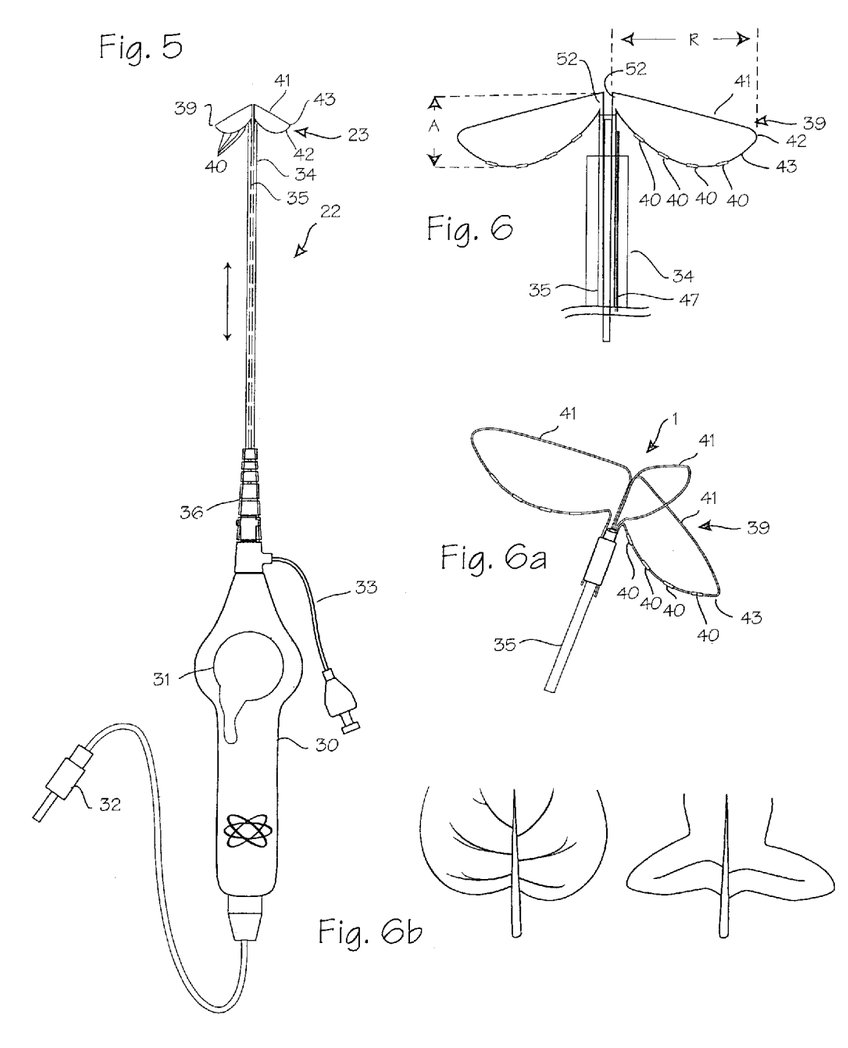
FIG. 5 illustrates the atrial sensing and ablation catheter of FIG. 2 with the electrode array in its expanded configuration.
FIGS. 6 and 6a is an enlarged view of the electrode array in its expanded configuration.
FIG. 6b illustrates the meaning of the terminology which precisely defines the electrode array of FIGS. 5 and 6

FIG. 3 is an enlarged view of the distal portion of the catheter of FIG. 2. The electrode array 23 comprises a number of resiliently biased arms 39 which each carry a number of electrodes 40. An array of three arms, each of which carry four electrodes, is suitable for use in the atria. The arms each comprise a wire (preferably a flat wire) with a distal section 41, a proximal section 42 and an intervening bend section 43. The electrodes are placed on the proximal sections. The proximal end of each arm is fixed to the inner catheter tube 35. The distal end of each arm is fixed to the floating tube (or pin) 44. This floating tube is retained within the inner catheter tube, but is free to slide longitudinally within the inner catheter tube. The necessary electrical wires 45 and 46 which connect the electrodes to the control system run from each electrode proximally along the arm (and through any intervening electrodes), and enter the lumen of the floating tube 44 and then run proximally through the inner catheter tube and into the catheter handle. (Additional wires for temperature sensing thermistor or thermocouples may be included.) The wires are looped within the handle to provide the distension necessary for the resilient deployment of the electrode array as illustrated in FIG. 5. A steering pull wire 47 is secured to the distal end of the inner catheter tube. The pull wire runs proximally to the steering control knob in the proximal handle, and is operably connected to the control knob so that rotation of the control knob pulls the pull wire to effectuate steering of the distal end of the device. The outer catheter tube is sufficiently flexible so that it is steered by deflection of the inner catheter tube. The materials used for each component are selected to provide the suitable flexibility, column strength and steerability. The outer catheter tube 34 may comprises nylon, polyester or other suitable polymer, and the inner catheter tube 35 comprises a stainless steel coil covered in shrink tubing to provide tensile strength. The electrode arms 39 comprise flat nitinol wires. The floating tube 44 comprises a stainless steel coil. The floating tube may be disposed over the inner catheter if accommodations are made for proximal fixation of the proximal arm segments to the inner catheter, such as placing the fixation points proximally on the inner catheter or providing slots on the proximal portion of the floating tube. The electrode wires may be disposed on or in the wall of the inner catheter, rather than passing through the lumen of the inner catheter as shown in the Figures.

Figure 4:
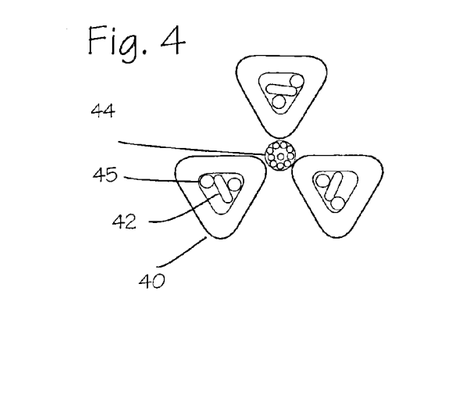
FIG. 4 is a cross-section of the distal portion of the catheter of FIG. 2.

FIG. 4 is a cross-section of the proximal portion of the catheter of FIG. 2. At this cross section, an electrode 40 is mounted on each arm 39. These electrodes will be located on the proximally facing portion of the deployed array as shown in FIGS. 5 and 6. The electrodes are tubes of triangular cross section, with tissue contacting faces directed radially outwardly from the catheter. The electrode wires 45, which are connected to the inside electrodes, run through the outer electrodes on their route to the floating tube. The electrode wires 46 are fixed to the inner wall of the outer electrode. As shown in this view, the electrodes are collapsed upon the floating tube 44, and due to the triangular shape they are securely packed within the outer catheter tube 34. The floating tube 44 also houses the various electrode wires 45 and 46.

FIGS. 5 and 6 illustrate the atrial sensing and ablation catheter of FIG. 2 with the electrode array in its expanded configuration. The outer catheter tube 34 has been withdrawn proximally over the catheter inner tube, allowing the array arms 39 to expand to create array elements defining a substantially cordate or hastate proximal outline. The term cordate is used as it is in botany to describe a leaf with a base (where the leaf attaches to the stem) which is heart-shaped, having rounded lobes at the base which arch proximally away from the tip and then curve distally toward the tip of the leaf, as shown in FIG. 6b. The term hastate is also adopted from botany, and refers to proximally tending lobes with slightly curved proximal outlines and sharply bending tips, also as shown in FIG. 6b. In the array shown in FIGS. 5 and 6, the base of the array (the proximal portion analogous to the base of a leaf) is heart-shaped, having rounded lobes at the base which arch proximally away from the base and then curve outward and distally toward the tip of the array. Each proximal arm segment resiliently bends radially outwardly from the proximal connection with the inner catheter tube, bending sharply in the proximal direction before arching outwardly and distally, while each distal arm segment bends radially inwardly from the bend portion toward the longitudinally axis of the catheter.

The electrode array includes a number electrodes 40 mounted on the proximal section 42 of each array arm, and the distal section 41 need not have any electrodes disposed on it, as is shown. The overall shape of each arm is elongate on an axis perpendicular to the long axis of the catheter, having a radial length R which is several times the axial length A.

The resilient expansion of the electrode array pushes the floating tube 44 proximally into the inner catheter tube. When the outer catheter tube is pushed distally over the electrode array, the distal electrode arms will be forced distally, as the proximal segments are compressed inwardly starting from the proximal end, to first splay the distal segments toward and through a perpendicular relationship with the floating tube such that the joint between the arms and the floating tube is distal to the bend point, while drawing the floating tube distally within the inner catheter tube.

Figure 7:
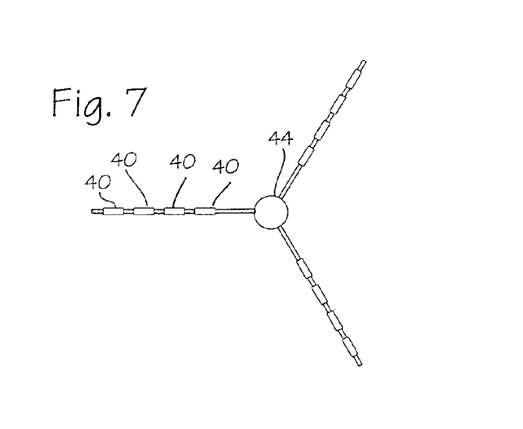
FIG. 7 is an end view of the electrode array in its expanded configuration.
Figure 7A:
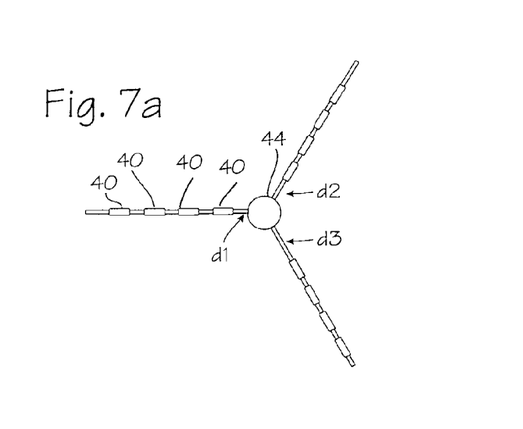
FIG. 7a is an end view of the electrode array, with an asymmetric arrangement of electrodes, in its expanded configuration.

FIG. 7 is a proximal end view of the electrode array in its expanded configuration. In this view, the three-arm array is fully expanded resiliently. The array provides four electrodes on each of three arms evenly distributed about the floating tube 44. The electrode wires 45 and 46 (shown in FIG. 3) extend inwardly from the electrodes and run proximally down the floating tube. The arms are each separated from the adjacent arms by about 120°. The array, when deployed and flattened as shown, is preferably about 15 to 30 mm in diameter (to the outer extent of the arm), with each distal arm segment 41 being about 7.5 to 15 mm long. The diameter of the electrode group (from the center to the outer extent of the electrodes) is preferably about 2 to 30 mm. The wire width is preferable about 0.26 mm, and the distal face of the electrodes is preferably about 1 to 2 mm wide and 2 to 3 mm long (the illustrated electrodes are 2 mm wide and 1.6 mm wide). The electrode array can comprise any number of arms, and each arm can carry any number of electrodes, though the three arm array, with dimensions described above, is well suited for the septal wall ablation therapy. FIG. 7a is an end view of the electrode array, with an asymmetric arrangement of electrodes, in its expanded configuration. In this embodiment, each electrode is 2 mm long, and is fixed to the array arm with a 2 mm gap between adjacent electrodes. The inner electrode of the first set of electrodes 40a is placed at a distance of 2 mm (indicated by item d1) from the inner catheter tube 35 and each of the additional electrodes are placed with 2 mm gaps between each electrode, while the inner electrode of the second set of electrodes 40b is placed at a distance of 4 mm (indicated by item d2) from the inner catheter tube 35 and each of the additional electrodes are placed with 2 mm gaps between each electrode, and the inner electrode of the third set of electrodes 40c is placed at a distance of 6 mm (indicated by item d3) from the inner catheter tube 35 and each of the additional electrodes are placed with 2 mm gaps between each electrode. With the electrodes arranged in this asymmetric pattern on each of the otherwise symmetrical array arms, rotation of the array after ablation in one position will be less likely to result in seating the electrodes directly on a previously ablated section of the septal wall.

Figure 8:
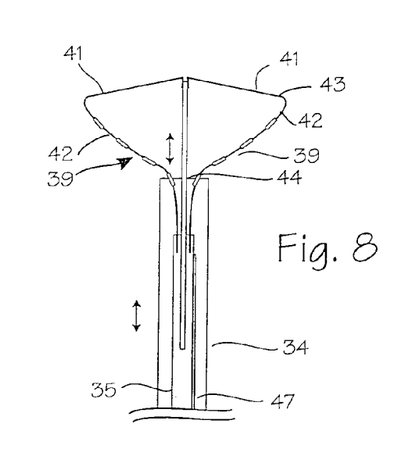
FIGS. 8 and 9 illustrate the mechanism of recapture of the electrode array of the atrial ablation catheter.
Figure 9:
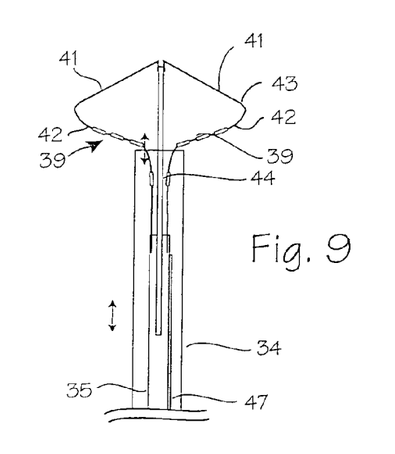

FIGS. 8 and 9 illustrate the mechanism of recapture of the electrode array. When the outer catheter tube 34 is pushed distally over the inner catheter tube 35 and the electrode array, the distal electrode arms 41 will be forced distally, as the proximal segments 42 are compressed inwardly starting from the proximal end, as shown in FIG. 8. This initially splays the distal segments toward a perpendicular relationship with the floating tube as shown in FIG. 8. As the outer catheter tube is translated further distally, such that the joint between the arms and the floating tube is distal to the bend point, the distal arm segments become further splayed, such that they are distal to the proximal arms segments. Because the distal arm segments are fixed to the floating tube, their movement distally draws the floating tube distally within the inner catheter tube. The array is completely captured when the outer catheter tube is translated fully forward to resume the position shown in FIGS. 2 and 3. As can be seen from the illustration, the bend sections provide a means for rotatably joining the distal arm segment to the proximal arm segment, and other suitable mechanisms, such as hinges, may be used instead.

Figure 10:
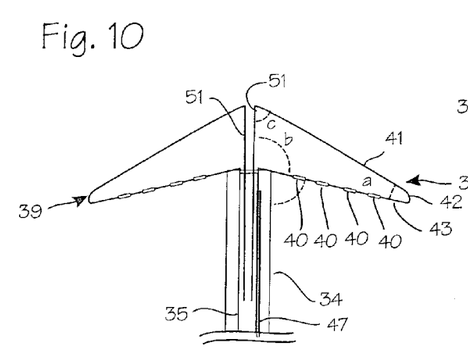
FIGS. 10 and 10a illustrates an alternate geometry of the septal wall array.
Figure 10A:
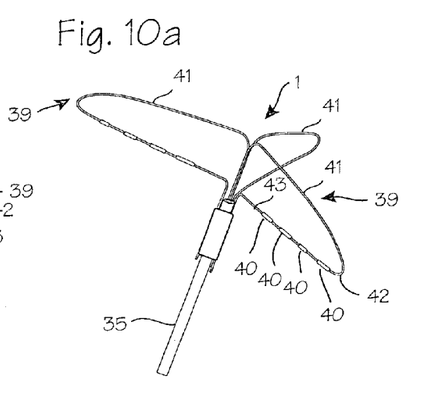
Figure 10B:
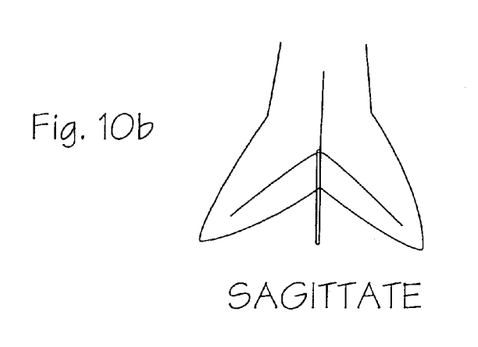

FIGS. 10 and 10a illustrate an alternate geometry of the septal wall array. The outer catheter tube 34 has been withdrawn proximally over the catheter inner tube, allowing the array arms 39 to expand to create array elements defining a substantially sagittate proximal outline. We use the term sagittate as that term is used in botany, where it describes a leaf with a base (where the leaf attaches to the stem) which is arrow-shaped (the back end of the arrow), having sharply triangular lobes with generally straight sides at the base which bend proximally away from the tip and then sharply turn distally toward the tip of the leaf, as shown in FIG. 10b.

Here, the array arms have sharply triangular lobes at the base which bend proximally away from the catheter and then sharply turn distally toward the tip of the array. Each proximal arm segment resiliently bends radially outwardly from the proximal connection with the inner catheter tube, bending sharply in the proximal direction, while each distal arm segment bends radially inwardly from the bend portion toward the longitudinally axis of the catheter. The floating tube 44 of FIG. 6 need not be used, as in this example the array distal arm segments are joined at their extreme distal ends to floating pins 51 which comprise proximally running segments that enter the inner catheter tube to provide the floating attachment of the distal arm segments to the catheter body. (Thus both floating pin or arm extensions, or the floating tube, and other suitable means, may be used to fix the distal end of the electrode arms in a radially central area while leaving the distal ends of the electrode arms freely translatable along the catheter longitudinal axis.) The electrode array can be restrained within the outer catheter tube, released and recaptured by sliding the outer catheter proximally or distally.

Figure 11:
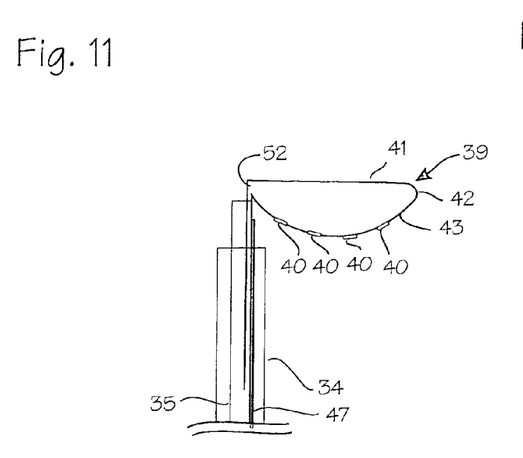
FIGS. 11, 12 and 13 illustrate additional alternative geometries of the array.
Figure 12:
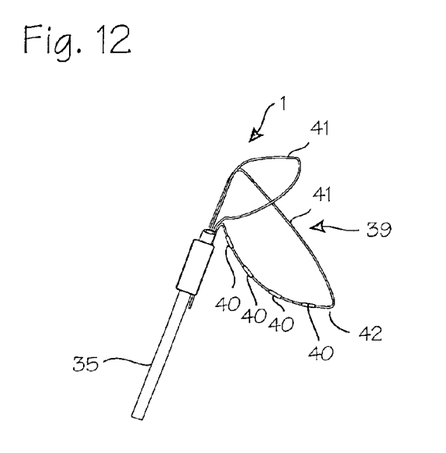
Figure 13:
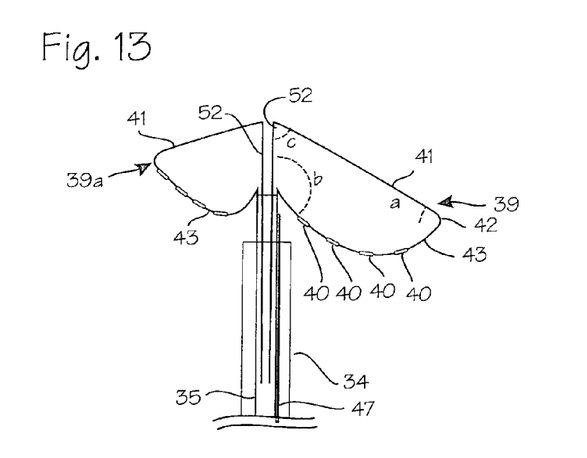

FIGS. 11, 12 and 13 illustrate additional alternative geometries of the array. In each device, the overall shape of the array arms may be as shown in any of the previous figures, but the array is asymmetrical or oblique. In FIG. 11, the array consists of a single arm 39, while in FIG. 12 the array comprises two arms disposed at a slight angle to each other, so that the array is radially asymmetrical. In FIG. 13, the array comprises an array arms 39 and 39a which are of substantial different sized, resulting in an oblique arrangement. Again, the term oblique is borrowed from botany, where it refers to leaves with lopsided proximal lobes, very similar to the lopsided proximal outlines of the array arms in FIG. 13. These arrays may be used where the anatomy of a particular patient's atrium demands, as where the fossa ovalis is positioned very near an upper or lower wall which would prevent full deployment of a symmetrical array.

Figure 14:
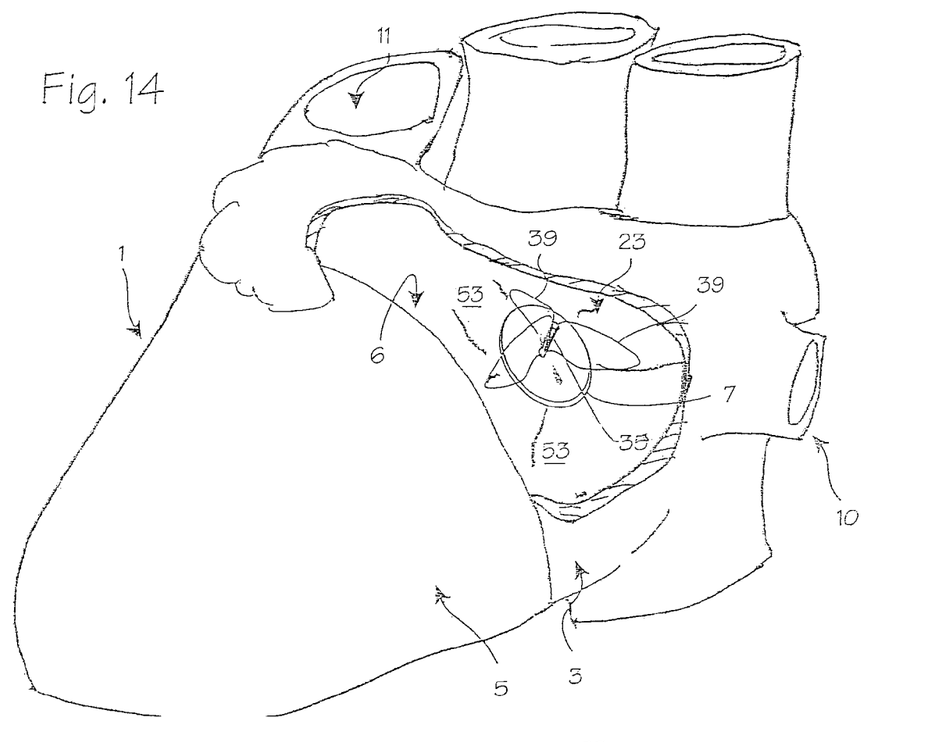
FIGS. 14 and 15 illustrate the method of using the device of to treat the septal wall of the left atrium.
Figure 15:
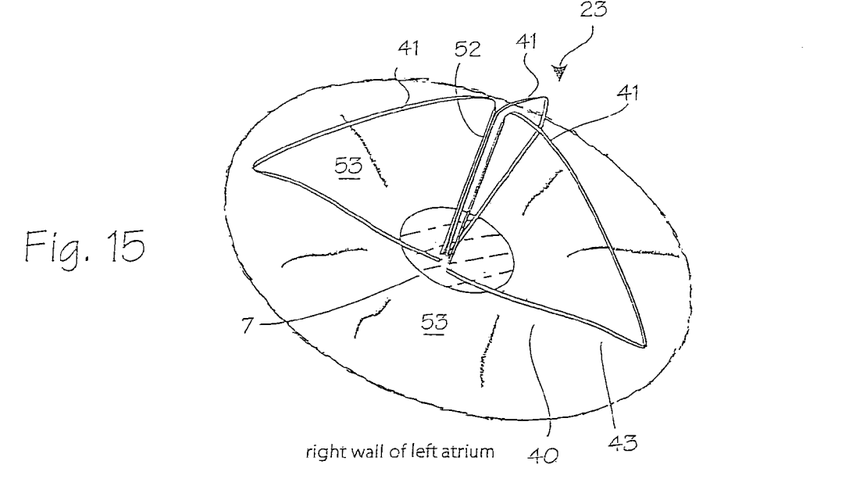

FIGS. 14 and 15 illustrate the method of using the device of FIG. 6 or 10. FIG. 14 shows the heart 1 fro the left side, showing the left atrium 3, the left ventricle 5, pulmonary veins 10, pulmonary artery 11. The left atrium is shown in a cutaway view, in which the atrial septum 6 and its left atrial surface 53 and the fossa ovalis 7 are shown. To treat arrhythmogenic foci, drivers or rotors on the septal wall near the fossa ovalis, the distal end of the catheter of Figure FIG. 6 or 10 is inserted through the fossa ovalis (via the transeptal approach from the right atrium). Thereafter, the outer catheter is withdrawn, so that the electrode array arms 39 resiliently expand to the configuration in which the proximal arm segments are substantially parallel or slightly reflexed relative to the long axis of the catheter. As shown in FIG. 15, to engage the septal wall, the electrode array is pulled proximally into contact with the septal wall, by pulling proximally on the catheter inner tube 35. As shown, the array will deform, forcing the distal arm segments 41 to splay distally, drawing the floating posts or pins 51 distally in response to the deformation of the array, while at the same time resiliently biasing the proximal arm segments 42 and the electrodes 40 against the septal wall 53 of the left atrium.

After contact has been established between the atrium wall and the electrode array, the operator will analyze electrical signals detected by the electrodes to determine if the array has been placed over an arrhythmogenic focus. If it has, the operator may energize any of the electrodes, as appropriate, to ablate the focus. Bipolar RF energy may be applied between pairs of the electrodes, or monopolar energy may be applied to any of the electrodes (grounded to the surface electrode or a return electrode located proximally on the catheter body). The array may moved off the septal wall, rotated slightly, and reseated against the septal wall to test and treat the entire area surrounding the fossa ovalis with just a few array arms (alternatively, the array may be provided with many arms, such that the electrode density it sufficient to find an ablate all significant foci within its footprint). Linear lesions may be created using the electrodes along a single proximal arm, operating the electrodes in bipolar mode, and other therapeutic lesions may be created using electrodes pairs established between the electrodes of one arm and the electrodes of another arm, operating such pairs in bipolar mode, or operating electrodes in conjunction with return electrodes in a monopolar mode.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. An ablation catheter comprising:
   a catheter having a distal end adapted for insertion into the left atrium of patient through the Fossa ovalis;
   an electrode array comprising at least one resilient arm, each arm having a proximal arm segment and a distal arm segment extending distally from an outer end of the proximal arm toward the center line of the catheter, such that the proximal arm segment extends from a longitudinal axis of the catheter such that a proximal portion of the proximal arm segment forms an acute angle with the longitudinal axis of the catheter;
   a plurality of electrodes disposed on each of the proximal arm segments of the array;
   wherein the proximal arms are arcuate, and extend outwardly and proximally and then curve distally such that the arcuate shape of the proximal arms is configured to, in use, substantially conform and ablate a septal wall.

2. An ablation catheter of claim 1, wherein the proximal arm segments are curved in a cordate arc.

3. An ablation catheter of claim 1, wherein the proximal arm segment is curved in a hastate arc.

4. An ablation catheter of claim 1, wherein the proximal arm segment and distal arm segment define a sagittate lobe.

5. An ablation catheter of claim 1, wherein each distal arm segment is characterized by a proximal to catheter shaft end and a distal to catheter shaft end; further comprising
   a proximally extending pin fixed at the distal end of the distal arm and extending into the catheter, said pin being longitudinally slidable relative to the catheter.

6. The catheter of claim 5, wherein the position and flexibility of a distal portion of the proximal arm segment are controllable by the position of the longitudinally-slidable pin.

7. An ablation catheter of claim 1, further comprising:
   a plurality of resilient arms on the array, wherein each of the plurality of arms is substantially the same size and shape, and the resilient arms are uniformly distributed radially about the axis of the catheter.

8. An ablation catheter of claim 1, further comprising:
   a plurality of resilient arms on the array, wherein at least one of the plurality of resilient arms is substantially different in size or shape than other arms in the array.

9. The catheter of claim 1, wherein the position and flexibility of a distal portion of the proximal arm segment are controllable by the position of a distal end of the electrode arm.

10. An ablation catheter of claim 1, further comprising:
    a plurality of resilient arms on the array unevenly distributed such that several arms are concentrated in a small radial section about the axis of the catheter, and a significant radial section is vacant.

11. An ablation catheter comprising:
    an outer catheter tube;
    an inner catheter tube (rod) slidably disposed within the outer catheter tube, said inner catheter tube having a distal end adapted for insertion into a vessel of the body;
    an electrode array comprising a plurality of resilient arms, each arm having a proximal arm segment fixed to the inner catheter tube and a distal arm segment extending distally from an outer end of the proximal arm, such that the proximal arm segment extends from a longitudinal axis of the inner catheter tube such that a proximal portion of the proximal arm segment forms an acute angle with the longitudinal axis of the inner catheter tube;
    a plurality of electrodes disposed on each of the proximal arm segments of the array;
    means for fixing the distal end of the electrode arms in a radially central area while leaving the distal ends of the electrode arms freely translatable along the catheter longitudinal axis
    wherein the proximal arm segments are curved in a cordate arc shape;
    such that the cordate shape of the proximal arms is configured to, in use, substantially ablate a septal wall.

12. The catheter of claim 11, wherein the position and flexibility of a distal portion of the proximal arm segment are controllable by the position of a distal end of the electrode arm.

13. An ablation catheter comprising:
    an outer catheter tube;
    an inner catheter tube slidably disposed within the outer catheter tube, said inner catheter tube having a distal end adapted for insertion into a vessel of the body;
    an electrode array comprising a plurality of resilient arms, each arm having a proximal arm segment fixed to the inner catheter tube and a distal arm segment extending distally from an outer end of the proximal arm, such that the proximal arm segment extends from a longitudinal axis of the inner catheter tube such that a proximal portion of the proximal arm segment forms an acute angle with the longitudinal axis of the inner catheter tube;
    a plurality of electrodes disposed on each of the proximal arm segments of the array;
    means for fixing the distal end of the electrode arms in a radially central area while leaving the distal ends of the electrode arms freely translatable along the catheter longitudinal axis
    wherein the proximal arm segments are curved in a hastate arc shape;
    such that the hastate shape of the proximal arms is configured to, in use, substantially ablate a septal wall.

14. The catheter of claim 13, wherein the position and flexibility of a distal portion of the proximal arm segment are controllable by the position of a distal end of the electrode arm.

15. An ablation catheter comprising:
    an outer catheter tube;
    an inner catheter tube slidably disposed within the outer catheter tube, said inner catheter tube having a distal end adapted for inscription into a vessel of the body;

an electrode array comprising a plurality of resilient arms, each arm having a proximal arm segment fixed to the inner catheter tube and a distal arm segment extending distally from an outer end of the proximal arm, such that the proximal arm segment extends from a longitudinal axis of the inner catheter tube such that a proximal portion of the proximal arm segment forms an acute angle with the longitudinal axis of the inner catheter tube;

a plurality of electrodes disposed on each of the proximal arm segments of the array;

means for fixing the distal end of the electrode arms in a radially central area while leaving the distal ends of the electrode arms freely translatable along the catheter longitudinal axis wherein the proximal arm segments define a sagittate outline relative to the base of the electrode array;

such that the sagittate outline of the proximal axis is configured to, in use, substantially ablate a septal wall.

16. The catheter of claim 15, wherein the position and flexibility of a distal portion of the proximal arm segment are controllable by the position of a distal end of the electrode arm.

17. An ablation catheter comprising:
an outer catheter tube;
an inner catheter tube slidably disposed within the outer catheter tube, said inner catheter tube having a distal end adapted for insertion into a vessel of the body;
an electrode array comprising a plurality of resilient arms, each arm having a proximal arm segment fixed to the inner catheter tube, such that the proximal arm segment extends from a longitudinal axis of the inner catheter tube such that a proximal portion of the proximal arm segment forms an acute angle with the longitudinal axis of the inner catheter tube, and a distal arm segment, extending distally from an outer end of the proximal arm and having a proximally tending extension extending proximally from the distal end of the distal arm segment, said extension being longitudinally translatable within the inner catheter tube, whereby the electrode array may be compressed by longitudinal translation of the outer catheter tube relative to the inner catheter tube, and the proximally tending extension longitudinally translates relative to the inner tube to accommodate longitudinal movement of the distal end of the resilient arms in response to compression of the electrode array;
a plurality of electrodes disposed on each of the proximal arm segments of the array, the electrodes of the plurality disposed so as to substantially ablate a septal wall;
means for fixing the distal end of the electrode arms in a radially central area while leaving the distal ends of the electrode arms freely translatable along the catheter longitudinal axis.

18. The catheter of claim 17, wherein the position and flexibility of a distal portion of the proximal arm segment are controllable by the position of the proximally tending extension.

19. The ablation catheter of claim 17, wherein a floating tube is disposed at least partially within the distal end of the inner catheter tube.

20. The ablation catheter of claim 19, wherein the electrode array is resiliently movable from a small diameter configuration and a large diameter configuration, and in the large diameter configuration each proximal arm segment resiliently bends radially outwardly from the inner catheter tube, and each distal arm segment bends radially inwardly and proximally toward the longitudinal axis of the catheter from a bend point connecting the proximal arm segment to the distal arm segment, and said electrode arms are further deformable upon pressing the array against a surface to position the distal arm segments into a substantially planar arrangement.

21. The ablation of claim 20, further comprising a control wire fixed to the floating tube and operable from the proximal end of the catheter to pull the floating tube proximally.

22. The ablation catheter of claim 19, wherein the floating tube comprises a stainless steel coil.

23. The ablation catheter of claim 17, wherein the electrode array is resiliently movable from a small diameter configuration to a large diameter configuration, and in the large diameter configuration each proximal arm segment resiliently bends radially outwardly from the inner catheter tube, and each distal arm segment bends radially inwardly toward the longitudinal axis of the catheter from a bend point connecting the proximal arm segment to the distal arm segment, creating an acute angle between each distal arm segment and its associated proximal arm segment.

24. The ablation catheter of claim 17, wherein the electrode array is resiliently movable from a small diameter configuration and a large diameter configuration, and in the large diameter configuration each proximal arm segment resiliently bends radially outwardly from the inner catheter tube, and each distal arm segment bends radially inwardly and proximally toward the longitudinal axis of the catheter from a bend point connecting the proximal arm segment to the distal arm segment.

25. The ablation catheter of claim 23, 24 or 20, wherein, in the small diameter configuration, the distal arm segments are restrained within a segment of the outer catheter tube which is distal to the proximal arm segments, and extend distally from the bend point.

26. The ablation catheter of claim 23, 24 or 20, wherein, in the small diameter configuration, the distal arm segments are folded inwardly so as to be disposed proximate the proximal arm segments and extend proximally from the bend point.

27. An ablation catheter comprising:
a cather;
an electrode army disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments, wherein the proximal arms are arcuate, and such that the arcuate shape of the proximal arms is configured to, in use, substantially ablate a septal wall;
wherein at least one electrode is disposed on each of the proximal arm segments of the array;
wherein the distal arm segments tend proximally from the bend point in the large diameter configuration and tend distally from the bend point in the small diameter configuration: and
further comprising a floating tube slidably disposed within the catheter and fixed to the distal arm segments.

28. An ablation catheter comprising:
a catheter;
an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments, wherein the proximal arms are arcuate, and such that the arcuate shape of the proximal arms is configured to, in use, substantially ablate a septal wall;

wherein at least one electrode is disposed on each of the proximal arm segments of the array;

wherein the distal arm segments tend proximally from the bend point in the large diameter configuration and tend distally from the bend point in the small diameter configuration; and further comprising a floating tube slidably disposed within the catheter and fixed to the distal arm segments, wherein the tube comprises a coil.

29. An ablation catheter comprising:
a catheter;
an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments, wherein the proximal arms are arcuate, and such that the arcuate shape of the proximal arms is configured to, in use, substantially ablate a septal wall;
wherein at least one electrode is disposed on each of the proximal arm segments of the array;
wherein the distal arm segments tend proximally from the bend point in the large diameter configuration and tend distally from the bend point in the small diameter configuration; and
wherein, in the small diameter configuration, the distal arm segments are folded inwardly so as to be disposed proximate the proximal arm segments and extend proximally from the bend point.

30. An ablation catheter comprising:
a catheter;
an electrode array disposed on the distal end of the catheter, said electrode array comprising a plurality of resilient arms, each arm having a proximal arm segment and a distal arm segment resiliently or rotatably joined to each other at a bend point, whereby the electrode array may be retained in a small diameter configuration within the catheter and released to assume a large diameter configuration, wherein the large diameter configuration comprises the proximal arm segments bent radially outwardly from the catheter with the distal arm segments extending radially inwardly from the proximal arm segments, wherein the proximal arms are arcuate, and such that the arcuate shape of the proximal arms is configured to, in use, substantially ablate a septal wall;
wherein at least one electrode is disposed on each of the proximal arm segments of the array; and
further comprising:
a floating tube slidably disposed within the catheter and fixed to the distal arm segments, and further comprising a control wire fixed to the floating tube and operable from the proximal end of the catheter to pull the floating tube proximally.

31. A method of treating atrial fibrillation comprising:
providing a catheter having an electrode array disposed on the distal end thereof, said electrode array comprising:
a plurality of resilient arms, each arm having a proximal arm segment and a distal arm segment connected by a bend point, said arms being resiliently biased to bend at an acute angle at the bend points, and a plurality of electrodes disposed on each of the proximal arm segments;
wherein said electrode array has an expanded configuration in which each proximal arm segment resiliently bends radially outwardly from the catheter, and each distal arm segment bends radially inwardly toward the longitudinal axis of the catheter from the bend point, wherein the proximal arms are arcuate, and such that the arcuate shape of the proximal arms is configured to, in use, substantially ablate a septal wall;
restraining the electrode array in a small diameter configuration within the outer catheter tube;
inserting the electrode array into the left atrium of the heart of a patient;
withdrawing the outer tube from the electrode array, and allowing the electrode array to expand to its expanded configuration;
pulling the proximal arm segments of the electrode array against an area of the septal wall;
sensing electrical signals of the septal wall through the electrodes of the electrode array;
upon determining that the array is disposed over an arrhythmogenic focus in the septal wall, passing energy through the electrode array to ablate a portion of the septal wall;
moving the electrode array as desired to additional areas of the septal wall and repeating the sensing and abating steps as desired to treat atrial fibrillation.

32. A method of treating atrial fibrillation comprising:
providing a catheter comprising:
an outer catheter tube;
an inner catheter tube slidably disposed within the outer catheter tube, said inner catheter tube having a distal end adapted for insertion into a vessel of the body;
a floating tube slidably disposed relative to the inner catheter tube; and
providing an electrode array comprising:
a plurality of resilient arms, each arm having a proximal arm segment and a distal arm segment connected by a bend point, side arms being resiliently biased to bend at an acute angle at the bend points, and a plurality of electrodes disposed on each of the proximal arm segments, wherein the proximal arms are arcuate, and such that the arcuate shape of the proximal arms is configured to, in use, substantially ablate a heart septal wall;
fixing the proximal arm segments to the inner catheter tube;
fixing the distal arm segments to the floating tube;
restraining the electrode array in a small diameter configuration within the outer catheter tube;
inserting the electrode array into the left atrium of the heart of a patient;
withdrawing the outer tube from the electrode array, and allowing the electrode array to resiliently expand so that each proximal arm segment resiliently bends radially outwardly from the inner catheter tube, and each distal arm segment bends radially inwardly and proximally toward the longitudinal axis of the catheter from the bend point;

pulling the electrode array against an area of the heart septal wall to deform at least the proximal arm segments and contact the electrodes with the heart septal wall;

sensing electrical signals of the heart septal wall through the electrodes of the electrode array;

upon determining that the array is disposed over an arrhythmogenic focus in the septal wall, passing energy through the electrode array to ablate a portion of the heart septal wall;

moving the electrode array as desired to additional areas of the heart septal wall and repeating the sensing and abating steps as desired to treat atrial fibrillation.

33. The method of claim 31 or 32, further comprising the steps of:

providing a return electrode on the catheter, proximal to the electrodes of the electrode array;

pulling the electrode array against the septal wall of the left atrium of the heart to sense electrical signals;

operating at least one electrode of the array in monopolar mode in conjunction with the return electrode to ablate a portion of the posterior wall of the left atrium.

34. The method of claim 31 or 32, further comprising the steps of:

providing a return electrode on the catheter, proximal to the electrodes of the electrode array;

pulling the electrode array against an ostium of a pulmonary vein opening to the left atrium of the heart to sense electrical signals;

operating at least one electrode of the array in monopolar mode in conjunction with the return electrode to ablate a portion of the left atrium wall surrounding a pulmonary vein.

35. The method of claim 32, wherein the position and flexibility of a distal portion of the proximal arm segment are controllable by the position of the floating tube.

36. A method of forming an electrode array comprising:

providing a catheter comprising:

an outer catheter tube;

an inner catheter tube slidably disposed within the outer catheter tube, said inner catheter tube having a distal end adapted for insertion into a vessel of the body;

a floating tube slidably disposed relative to the inner catheter tube; and providing an electrode array comprising:

a plurality of resilient arms, each arm having a proximal arm segment and a distal arm segment connected by a bend point, side arms being resiliently biased to bend at an acute angle at the bend points, and a plurality of electrodes disposed on each of the proximal arm segments;

fixing the proximal arm segments to the inner catheter tube;

fixing the distal arm segments to the floating tube;

restraining the electrode array in a small diameter configuration within the outer catheter tube;

withdrawing the outer tube from the electrode array, and allowing the electrode array to resiliently expand so that each proximal arm segment resiliently bends radially outwardly from the inner catheter tube, and each distal arm segment bends radially inwardly and proximally toward the longitudinal axis of the catheter from the bend point, wherein the proximal arms are arcuate, and such that the arcuate shape of the proximal arms is configured to, in use, substantially ablate a surface;

pressing the electrode array against a surface to deform the proximal arm segments toward a substantially planar arrangement.

37. The method of claim 36, wherein the position and flexibility of a distal portion of the proximal arm segment are controllable by the position of the floating tube.

* * * * *